US00PP19695P2

(12) United States Plant Patent
Murakami

(10) Patent No.: US PP19,695 P2
(45) Date of Patent: Feb. 10, 2009

(54) ***SCOPARIA* PLANT NAMED 'SUNTUTUBU'**

(50) Latin Name: ***Scoparia* sp.**
Varietal Denomination: Suntutubu

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/079,287

(22) Filed: Mar. 25, 2008

(51) Int. Cl.
*A01H 5/00* (2006.01)

(52) U.S. Cl. ..... Plt./263.1

(58) Field of Classification Search ..... Plt./263.1, Plt./263

See application file for complete search history.

*Primary Examiner*—Annette H Para
(74) *Attorney, Agent, or Firm*—C. A. Whealy

(57) ABSTRACT

A new and distinct cultivar of *Scoparia* plant named 'Suntutubu', characterized by its upright and mounding plant habit; vigorous growth habit; freely branching habit; numerous small blue violet-colored flowers; long flowering period; and good garden performance.

1 Drawing Sheet

Botanical designation: *Scoparia* sp.
Cultivar denomination: 'Suntutubu'.

BACKGROUND OF THE INVENTION

The present invention relates to a new and distinct cultivar of *Scoparia,* botanically known as *Scoparia* sp. and hereinafter referred to by the name 'Suntutubu'.

The new *Scoparia* is a product of a planned breeding program conducted by the Inventor in Higashiomi, Shiga, Japan. The objective of the breeding program was to create new compact *Scoparia* cultivars with attractive flower coloration.

The new *Scoparia* originated from a cross-pollination made by the Inventor in May, 2004, in Higashiomi, Shiga, Japan, of a proprietary selection of *Scoparia* sp. identified as code number SCWB4, not patented, as the female, or seed, parent with a proprietary selection of *Scoparia* sp. identified as code number SCWB6, not patented, as the male, or pollen, parent. The new *Scoparia* was discovered and selected by the Inventor as a single flowering plant within the progeny of the stated cross-pollination in a controlled environment in Higashiomi, Shiga, Japan.

Asexual reproduction of the new *Scoparia* by vegetative cuttings in a controlled environment in Higashiomi, Shiga, Japan since September, 2005, has shown that the unique features of this new *Scoparia* are stable and reproduced true to type in successive generations.

SUMMARY OF THE INVENTION

The cultivar Suntutubu has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Suntutubu'. These characteristics in combination distinguish 'Suntutubu' as a new and distinct cultivar of *Scoparia:*

1. Upright and mounding plant habit.
2. Vigorous growth habit.
3. Freely branching habit.
4. Numerous small blue violet-colored flowers.
5. Long flowering period.
6. Good garden performance.

Plants of the new *Scoparia* differ from plants of the female parent selection in the following characteristics:

1. Plants of the new *Scoparia* are shorter than plants of the female parent selection.
2. Plants of the new *Scoparia* have smaller flowers than plants of the female parent selection.
3. Plants of the new *Scoparia* and the female parent selection differ in flower color as plants of the female parent selection have light blue violet-colored flowers.

Plants of the new *Scoparia* differ from plants of the male parent selection in the following characteristics:

1. Plants of the new *Scoparia* are taller than plants of the male parent selection.
2. Plants of the new *Scoparia* flower earlier than plants of the male parent selection.
3. Plants of the new *Scoparia* and the male parent selection differ in flower color as plants of the male parent selection have dark blue violet-colored flowers.

Plants of the new *Scoparia* can be compared to plants of the cultivar USSCO10, disclosed in U.S. Plant Pat. No. 15,934. In side-by-side comparisons conducted in Higashiomi, Shiga, Japan, plants of the new *Scoparia* and the cultivar USSCO10 differed in the following characteristics:

1. Plants of the new *Scoparia* were shorter than plants of the cultivar USSCO10.
2. Plants of the new *Scoparia* were more mounding than plants of the cultivar USSCO10.
3. Plants of the new *Scoparia* had broader leaves than plants of the cultivar USSCO10.
4. Plants of the new *Scoparia* flowered earlier than plants of the cultivar USSCO10.

5. Plants of the new *Scoparia* had darker colored flowers than plants of the cultivar USSCO10.

BRIEF DESCRIPTION OF THE PHOTOGRAPHS

The accompanying colored photographs illustrate the overall appearance of the new *Scoparia,* showing the colors as true as it is reasonably possible to obtain in colored reproductions of this type. Colors in the photographs may differ slightly from the color values cited in the detailed botanical description which accurately describe the colors of the new *Scoparia.*

The photograph at the top of the sheet comprises a side perspective view of a typical flowering plant of 'Suntutubu' grown in a container.

The photograph at the bottom of the sheet is a close-up view of typical flowers, flower buds and leaves of 'Suntutubu'.

DETAILED BOTANICAL DESCRIPTION

The aforementioned photographs and following observations, measurements and values describe plants grown in Higashiomi, Shiga, Japan, under commercial practice during the early summer in an outdoor nursery with day temperatures averaging 23° C. and night temperatures averaging 13° C. After planting, plants had been growing for about four months when the photographs and description were taken. In the following description, color references are made to The Royal Horticultural Society Colour Chart, 2001 Edition, except where general terms of ordinary dictionary significance are used.

Botanical classification: *Scoparia* sp. cultivar Suntutubu.

Parentage:

*Female, or seed, parent.*—Proprietary selection of *Scoparia* sp. identified as code number SCWB4, not patented.

*Male, or pollen, parent.*—Proprietary selection of *Scoparia* sp. identified as code number SCWB6, not patented.

Propagation:

*Type.*—By vegetative cuttings.

*Time to initiate roots.*—About six days at 20° C. to 25° C.

*Time to produce a rooted young plant roots.*—About three weeks at 20° C. to 25° C.

*Root description.*—Fine, fibrous, fleshy; light brown in color.

*Rooting habit.*—Freely branching.

Plant description:

*Plant form/habit.*—Upright and mounded plant habit; vigorous growth habit. Freely branching habit, about 13 lateral branches develop per plant.

*Plant height.*—About 19.2 cm.

*Plant width* (*spread*).—About 34.6 cm.

*Lateral branches.*—Length: About 21.1 cm. Diameter: About 1.8 mm. Internode length: About 2 cm. Strength: Strong. Texture: Smooth, glabrous. Color: Close to 144A.

Foliage description:

*Arrangement.*—Whorled, simple; sessile.

*Length.*—About 1.4 cm.

*Width.*—About 2 mm.

*Shape.*—Lanceolate.

*Apex.*—Acute.

*Base.*—Cuneate.

*Margin.*—Entire.

*Texture, upper and lower surfaces.*—Smooth, glabrous.

*Venation pattern.*—Parallel.

*Color.*—Developing and fully expanded leaves, upper surface: Close to 137C; venation, close to 137C. Developing and fully expanded leaves, lower surface: Close to 138B; venation, close to 138B.

Flower description:

*Flower type/habit.*—Small single rotate flowers; flowers face mostly outwardly. Freely flowering habit with about 210 flowers developing per plant.

*Fragrance.*—Similar to anise.

*Natural flowering season.*—Long and continuous flowering habit from spring to late autumn in Higashiomi, Shiga, Japan. Flowers not persistent.

*Postproduction longevity.*—Flowers last about three to five days on the plant.

*Flower buds*—Height: About 4.8 mm. Diameter: About 2.1 mm. Shape: Ovoid. Color: Close to N88B.

*Flower diameter.*—About 1 cm.

*Flower depth.*—About 5 mm.

*Petals.*—Quantity per flower: Typically four in a single whorl; petals fused. Length: About 5.4 mm. Width: About 3.8 mm. Shape: Ovate. Apex: Obtuse. Margin: Entire. Texture, upper and lower surfaces: Smooth, glabrous. Color: Developing and fully expanded petals, upper surface: Close to 92A. Developing and fully expanded petals, lower surface: Close to 92A.

*Sepals.*—Quantity per flower: Typically five in a single whorl, fused at base; star-shaped calyx. Length: About 3.3 mm. Width: About 1.5 mm. Shape: Lanceolate. Apex: Acute. Base: Obtuse. Margin: Entire. Texture, upper and lower surfaces: Smooth, glabrous. Color, upper and lower surfaces: Close to 144A.

*Peduncles.*—Length: About 5 mm. Diameter: About 0.3 mm. Texture: Smooth, glabrous. Color: Close to 144A.

*Reproductive organs.*—Stamens: Quantity per flower: Typically four. Stamen length: About 3.2 mm. Anther shape: Ellipsoidal. Anther size: About 2.3 mm by 0.9 mm. Anther color: Close to 13B. Pollen amount: Scarce. Pollen color: Close to 13C. Pistils: Quantity per flower: One. Pistil length: About 4.4 cm. Stigma shape: Globose. Stigma color: Close to N88D. Style color: Close to N88D. Ovary color: Close to 144D.

*Seed/fruit.*—Seed and fruit development have not been observed.

Disease/pest resistance: Plants of the new *Scoparia* have not been noted to be resistant to pathogens and pests common to *Scoparia.*

Garden performance: Plants of the new *Scoparia* have been observed to have good garden performance and tolerate rain, wind and temperatures from about −1° C. to about 35° C.

It is claimed:

1. A new and distinct *Scoparia* plant named 'Suntutubu' as illustrated and described.

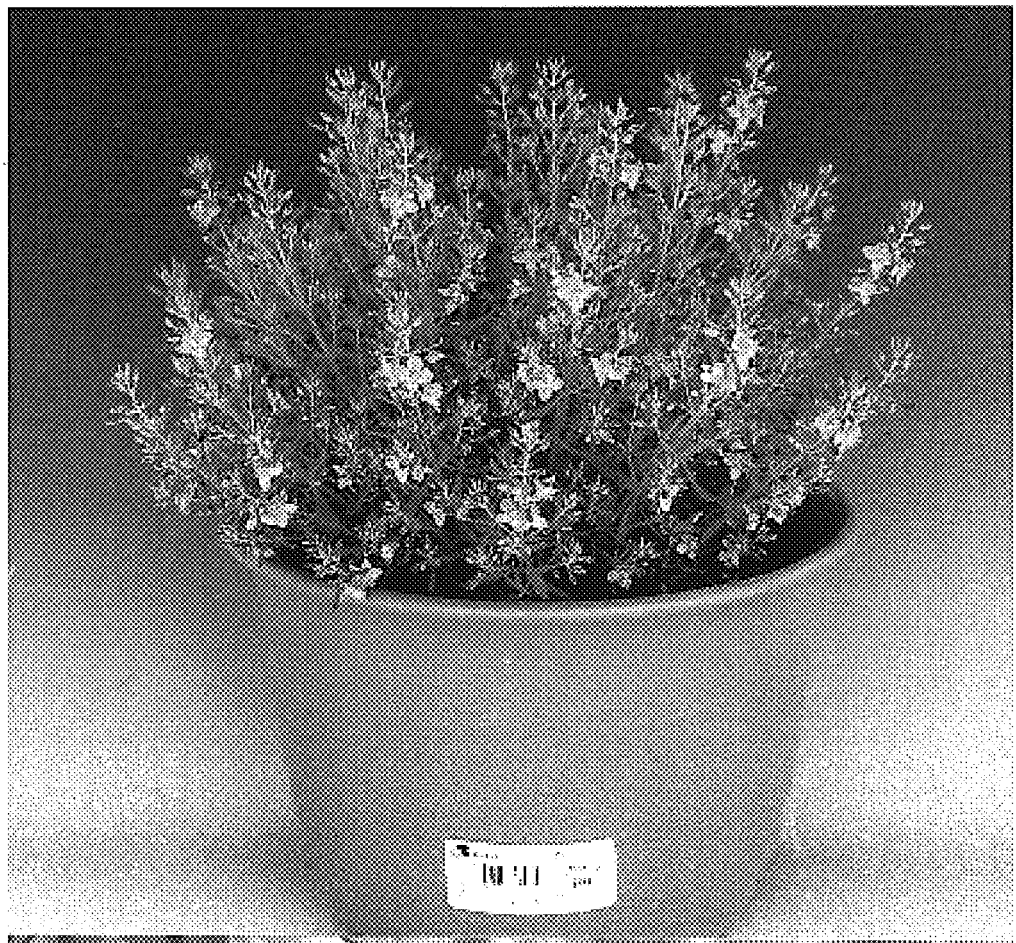
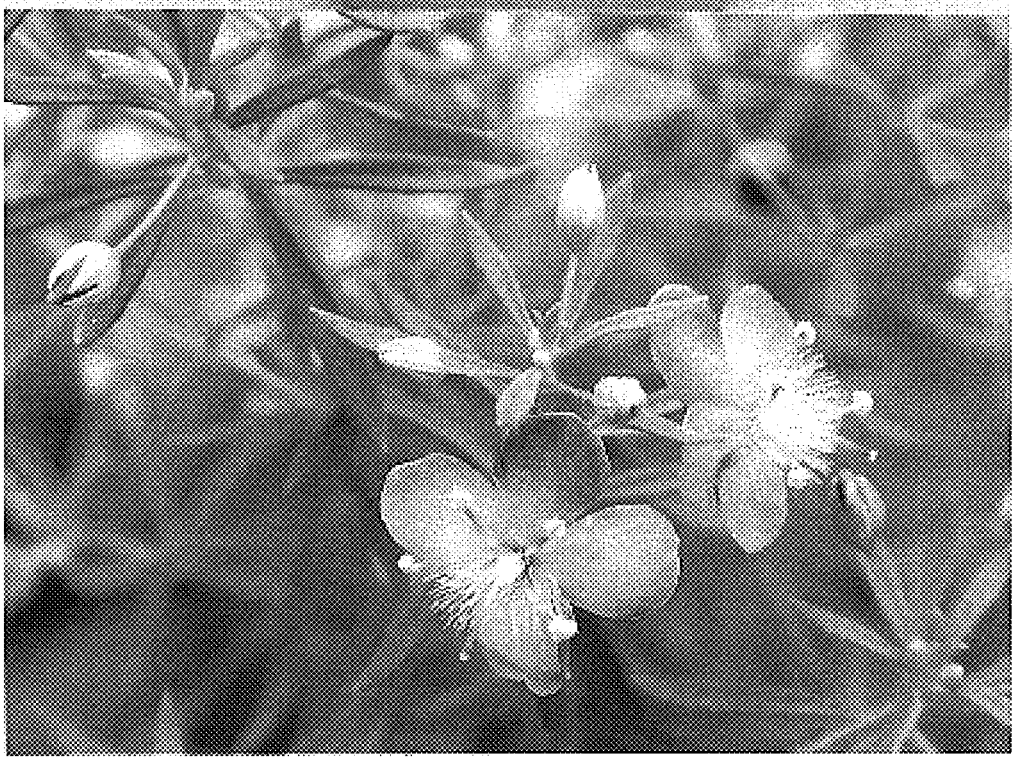

* * * * *